United States Patent [19]

Sagae et al.

[11] 4,299,217

[45] Nov. 10, 1981

[54] INTRAVASCULAR CATHETER

[75] Inventors: Kyuta Sagae, Tokyo; Susumu Tanabe, Sagamihara; Hiroshi Kamogawa, Fujinomiya, all of Japan

[73] Assignee: Terumo Corporation, Tokyo, Japan

[21] Appl. No.: 104,655

[22] Filed: Dec. 17, 1979

Related U.S. Application Data

[63] Continuation-in-part of Ser. No. 909,721, May 26, 1978, Pat. No. 4,217,895.

[51] Int. Cl.³ .................... A61M 5/00; A61M 25/00
[52] U.S. Cl. ................... 128/214.4; 128/240; 128/DIG. 16
[58] Field of Search ............. 128/214 R, 214.4, 221, 128/348, 240, DIG. 16, 347

[56] References Cited

U.S. PATENT DOCUMENTS

| | | | |
|---|---|---|---|
| 390,177 | 9/1888 | Lee | 128/349 R |
| 3,180,562 | 4/1965 | Wittes et al. | 128/214.4 X |
| 3,295,632 | 7/1965 | Plowiecki | 128/214.4 |
| 3,399,674 | 9/1968 | Pannier et al. | 128/214.4 |
| 3,699,961 | 10/1972 | Szpur | 128/218 M |
| 3,833,003 | 9/1974 | Taricco | 128/214.4 X |
| 3,851,646 | 12/1974 | Sarns | 128/348 X |
| 4,016,879 | 4/1977 | Mellor | 128/214.4 |
| 4,073,297 | 2/1978 | Kopp | 128/214.4 |
| 4,096,860 | 6/1978 | McLaughlin | 128/214.4 |
| 4,099,528 | 7/1978 | Sorenson et al. | 128/214.4 |

Primary Examiner—Stephen C. Pellegrino
Attorney, Agent, or Firm—Bacon & Thomas

[57] ABSTRACT

An intravascular catheter, comprising a hub having at least one branched tube mounted thereto apart from each other in the axial direction of the hub, a flexible double-walled tube having an inwardly tapered tip portion and consisting of an inner tube and an outer tube coaxial with the inner tube, providing an annular passageway between the outer wall of the inner tube and the inner wall of the outer tube and a needle removably inserted into the inner tube of the double walled tube. Further, the inner passageway has an opening at the tapered tip of the double-walled tube and the forward end of the annular passageway communicates with a bore or bores provided at the forward end portion of the outer tube excluding an upper portion thereof as defined by 20 in FIG. 6.

8 Claims, 12 Drawing Figures

INTRAVASCULAR CATHETER

CROSS-REFERENCE TO RELATED APPLICATION

This application is a continuation-in-part of our co-pending Ser. No. 909,721, filed May 26, 1978, now U.S. Pat. No. 4,217,895, and assigned to the same assignee as the parent application.

BACKGROUND OF THE INVENTION

This invention relates to an intravascular catheter useful for extracorporeal blood circulation through an artificial kidney, an artificial lung, or the like.

In a conventional blood dialyzing operation using an artificial kidney, a couple of needles are kept inserted respectively to each of the vein and artery of a patient for the suction and recovery of blood through the artificial kidney. In this case, the patient is obliged to suffer from a great deal of pain because two needles are stuck to his blood vessels. In addition, the life of the shunt serving to connect directly the artery and the vein tends to be shortened.

To overcome the above-noted drawbacks, a so-called "single needle system" has been proposed in which withdrawing from and returning to the body of the blood are effected by using a single needle. In this case, the opening-closing of a valve is performed electrically so as to enable the single needle to withdraw and return the blood alternately. The alternate operation naturally leads to a longer dialyzing time than for the case of using two needles, because shortening of the dialyzing time, will cause sharp and enlarged fluctuation in the internal pressure of the dialyzing circuit, giving bad influences to the patient. It should also be noted that the single needle system necessitates a particular machine for operating the circulation.

U.S. Pat. No. 4,073,297 discloses an extracorporeal blood circulation method utilizing a single-walled catheter or a double-walled catheter. In the U.S. Patent, the forward end portion of the catheter is provided with a plurality of bores extending the wall thereof and suitably apart from each other. In determining the locations of the bores, however, attentions are paid to only the mechanical strength of the catheter. In addition, one of the bores is located at the top portion of the wall when the catheter is horizontally disposed such that the tapered surface of the needle included in the catheter is faced vertically upward. It has been found, however, that the bore thus located gives rise to detrimental effects in operation of the catheter.

SUMMARY OF THE INVENTION

An object of this invention is to provide an intravascular catheter of a double-walled structure free from the drawbacks inherent in the conventional devices. Specifically, the catheter according to this invention necessitates sticking only once of a single needle into a blood vessel of a patient for achieving extracorporeal blood circulation, thereby alleviating the pain of the patient. Further, the invented catheter will enable an effective blood circulation equivalent to the conventional device using two needles. Still further, the catheter of this invention can be operated very easily.

According to this invention, there is provided an intravascular catheter, comprising a hub having an axial passage opening at both ends, an auxiliary passageway branched from the axial passageway;

a flexible double-walled tube having a solid and smoothly tapered tip portion and consisting of an inner tube extending into the axial passageway formed in the hub and providing a central passageway and an outer tube disposed in coaxial relation to the inner tube and with its outer surface merging smoothly with the tapered surface of said tip portion, thereby forming an annular passageway between the outer wall of the inner tube and the inner wall of the outer tube, the base edge of the inner tube being secured at an intermediate inner wall of the axial passageway between the auxiliary passageway and the rearward end of the axial passage, the base edge of the outer tube being fixed to the forward end of the hub so as to enable the annular passageway to communicate with the auxiliary passageway, and the central passageway having an opening at the tip of said tip portion and the forward end of the annular passageway having at least one bore provided at the forward end portion of the outer tube at the juncture of the outer tube and said tip portion; and a needle removably inserted into the central passageway formed in the inner tube such that the tip of the needle extends beyond the tapered tip of the double-walled tube and defines a smooth continuation of the tapered outer surface of said tip portion.

The location of said bore in the outer tube is preferably confined to such that when the axis of the catheter is disposed horizontally and the tapered surface of tip of the needle is faced virtically upward, the location of said bore should exclude the top curve portion of the outer tube in the cross section perpendicular to the axis of the catheter, which falls within ±30° around the center of the needle as measured from the top or middle point of the top curve portion.

DETAILED DESCRIPTION OF THE INVENTION

Figures 1, 2:
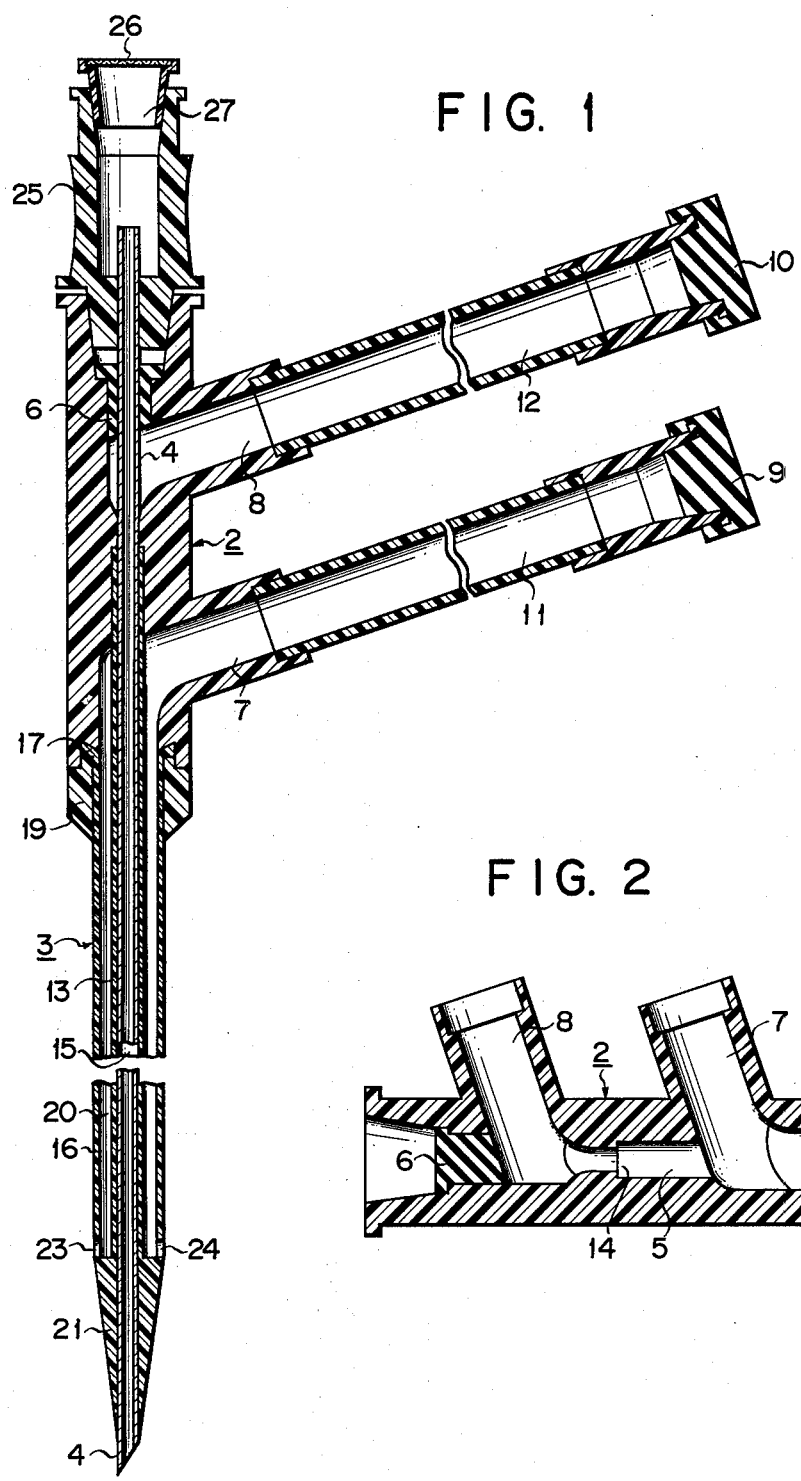
FIG. 1 is the longitudinal sectional view of an intravascular catheter according to one embodiment of this invention.
FIG. 2 is a longitudinal sectional view of the hub included in the catheter of FIG. 1.

As shown in FIG. 1, an intravascular catheter according to one embodiment of this invention comprises a hub 2, a double-walled tube 3 mounted to the tip portion of the hub 2 and having a tapered tip portion, and a needle 4 removably inserted into the double-walled tube 3. The hub 2, which is made of, for example, polycarbonate or polypropylene, is provided with an axial passageway 5 as shown in FIG. 2. The base end portion of the hub is sealed with a sealing member 6 formed of, for example, synthetic rubber so as to close the axial passageway 5, with the tip end of the axial passageway left open. Further, the hub 2 is provided with first and second auxiliary passageways 7 and 8 branched from the axial passageway 5. In general, first and second auxiliary tubes 11 and 12 formed of a transparent flexible plastic material and having caps 9 and 10 (see FIG. 1) removably mounted to the tips thereof are connected to the first and second auxiliary passageways 7 and 8, respectively.

The hub 2 may be formed by integral molding. Alternatively, it is possible to separate the hub into two sections, one section comprising the first auxiliary passageway 7 and the other section including the second auxiliary passageway 8. Namely, these two sections are molded separately and joined to each other later. The separate molding method is preferred because the subsequent work of fixing an inner tube 13 to the hub can be facilitated.

A double-walled tube 3 consisting of the inner tube 13 and an outer tube 16 is mounted to the forward end portion of the hub 2. Specifically, the base portion of the inner tube 13 is inserted into the axial passageway 5 of the hub to reach, for example, a stepped portion 14 provided between the first and second auxiliary blood passageways 7 and 8 and is bonded to the inner wall of the hub defining axial passageway 5 by using an adhesive or the like. Thus, the second auxiliary passageway 8 of the hub is allowed to communicate with a central passageway 15 formed in the inner tube 13. On the other hand, the base edge of the outer tube 16 is fixed to the forward end of the hub such that a flange 17 formed at the base edge of the outer tube is engaged with a stepped portion 18 of the hub, with a reinforcing member 19 disposed to ensure stable engagement between the flange 17 and the stepped portion 18. Naturally, the particular construction mentioned permits a sufficiently strong fixing of the outer tube to the hub.

The outer tube 16 completely surrounds that portion of the inner tube 13 which extends from the forward end of the hub 2 so as to have an annular passageway 20 formed between the outer wall of the inner tube and the inner wall of the outer tube. As shown in the drawing, the annular passageway 20 communicates with the first auxiliary passageway 7 of the hub. In other words, the axial passageway 5 formed in the hub 2 is divided by the presence of the inner tube 13 into two independent passageways communicating respectively with the first and second auxiliary passageways 7 and 8.

The inner and outer tubes 13 and 16 are bonded to each other at the forward end portions by fusion or the like. Further, the double-walled tube 3 consisting of these tubes 13 and 16 has a tapered tip portion 21. When a needle 4 is inserted through the central passageway formed in the inner tube 13, the shape of beveled tip of the double-walled tube 3 nearly conforms with the shape of the tip of the needle 4, thereby substantially avoiding the formation of a stepped portion therebetween for ease in passage through the skin and vascular wall.

At least one bore, for example, a pair of mutually facing bores 23, 24 as shown in FIG. 1, is formed in the tip portion of the outer tube 16 so as to enable the annular passageway to communicate with a blood vessel when the tip portion of the double-walled tube has been inserted into the blood vessel. It is preferred to provide the bores 23, 24 in a manner to communicate with the tip of the annular passageway 20 as shown in FIG. 1. Otherwise, the blood introduced into the tip portion of the annular passageway is held stationary, leading to coagulation of the blood.

It is also preferred to arrange such that a bore is not located at the top portion of the outer tube 16 when the tapered surface of the needle is faced upward. If a bore is located at the top portion of the outer tube as shown in, for example, FIGS. 1 and 5, the bore tends to be caught by the skin or blood vessel when the catheter is inserted into a blood vessel, resulting in increases in the resistance into a blood vessel, resulting in increases in the resistance to the catheter insertion into the blood vessel and in pain given to the patient as well as possible breakage of the bore. In addition, the bore tends to be closed partially by the inner wall of the blood vessel when the catheter is kept stuck to the blood vessel. In this case, the blood through the bore is reduced.

Figure 6:
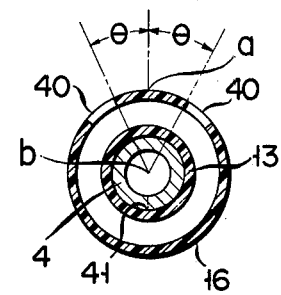
FIG. 6 is a cross sectional view showing the forward end portion of a catheter according to another embodiment of this invention.

The present inventors have found that the above-noted difficulties can be overcome if a prohibitive region within which a bore should not be formed is defined as shown in FIG. 6. Specifically, FIG. 6 shows a cross section perpendicular to the axis of a catheter horizontally disposed such that the tapered surface 4a of the needle 4 is faced upward, namely, the tip 41 of the tapered surface 4a constitutes the lowest portion of the needle 4. The prohibitive region is located at the top curve portion of the outer tube 16 in FIG. 6 and confined to such that the edge angles $\theta$ of the prohibitive region correspond $\pm 30°$ around the center (b) of the needle 4 as measured from the top point (a) of the top curve portion. Preferably, the prohibitive region should be confined to such that a line passing through the center of the uppermost bore and the center (b) of the needle 4 falls at an angle of at least 90° as measured in the same manner mentioned above, as shown in FIGS. 9 and 10.

Figure 5:
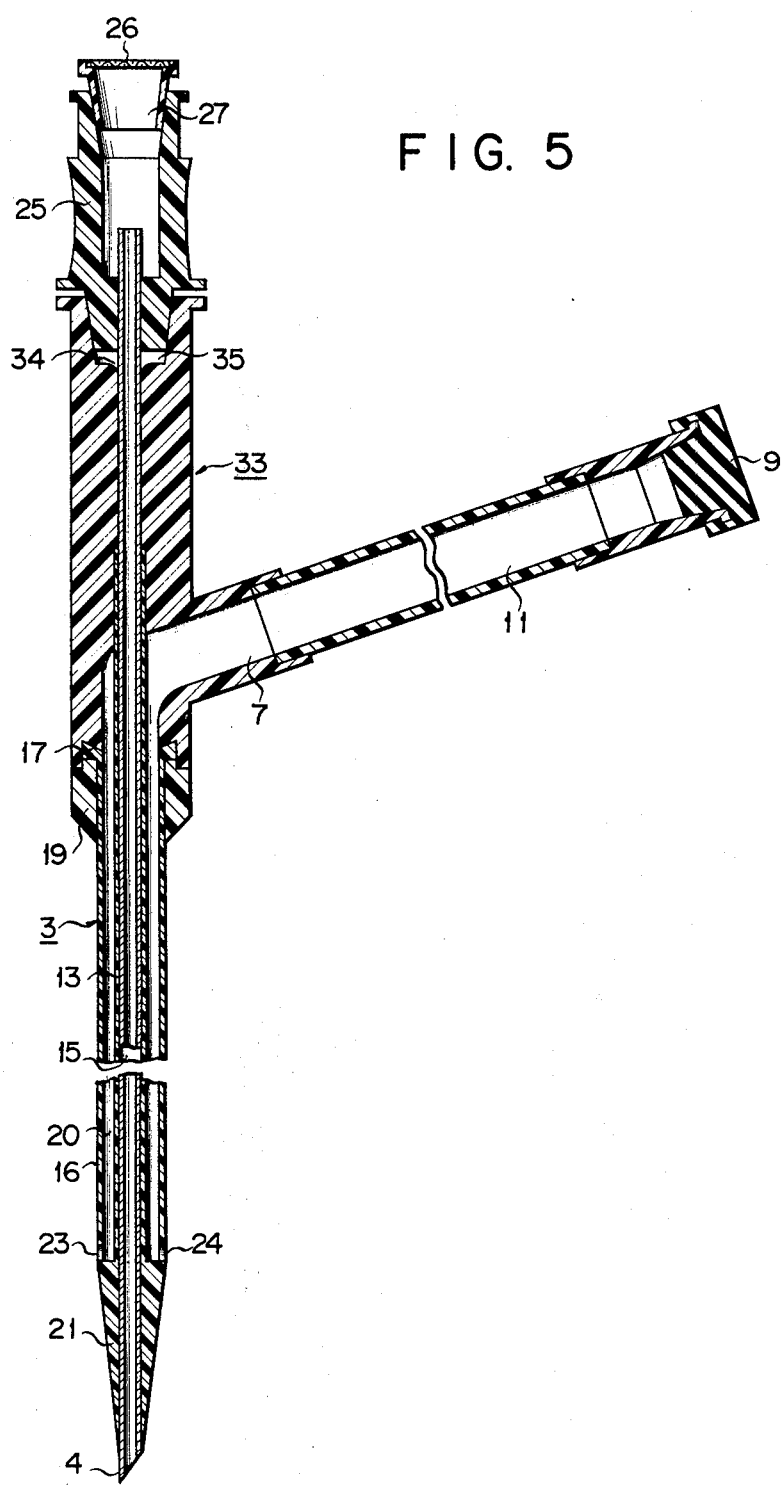
FIG. 5 is a longitudinal sectional view of an intravascular catheter showing another embodiment of this invention.
Figure 8:
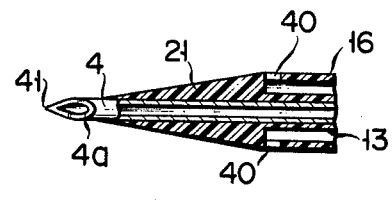
FIG. 8 is a cross sectional view along the line VIII—VIII of FIG. 7.
Figure 7:
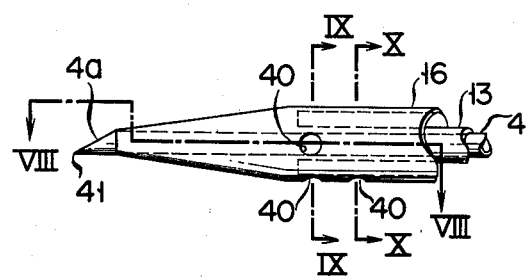
FIG. 7 is a side view showing the forward end portion of a catheter according to another embodiment of this invention.
Figure 9:
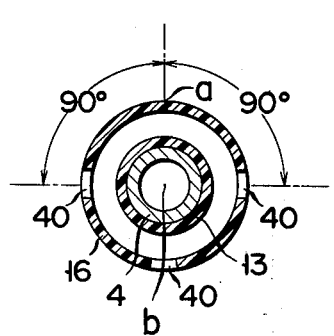
FIG. 9 is a cross sectional view along the line IX—IX of FIG. 7.
Figure 10:
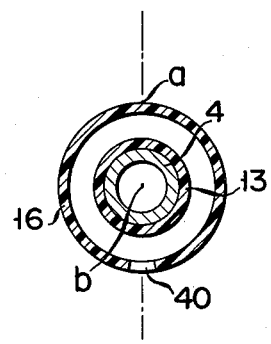
FIG. 10 is a cross sectional view along the line X—X of FIG. 7.

Specifically, FIGS. 7, 9 and 10 show that the bores 40 are located just sideways and at the bottom of the outer tube 16 when the tapered surface 4a of the needle 4 is faced upward unlike the arrangements of FIGS. 1 and 5. In FIG. 6, the bores 40 are located adjacent to the prohibitive region with $\theta$ of 30° mentioned previously.

The sum of the cross-sectional area of the bores provided in the wall of the outer tube should be at least as large as the cross-sectional area of the annular outer lumen. Although, there is no upper limit to the sum of the cross-sectional area of the bores, it is generally not required to be more than six times the cross-sectional area of the annular outer lumen.

Figure 11:
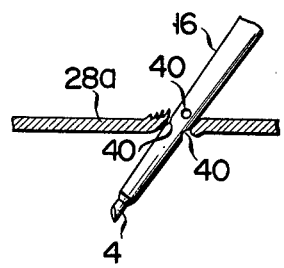
FIGS. 11 and 12 show how catheters differing from each other in the location of side bores are inserted into a blood vessel.
Figure 12:
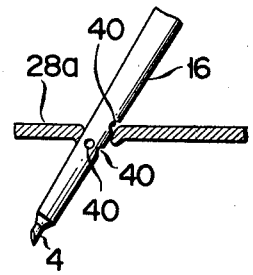

The following experiments were conducted in an attempt to show the merit produced by the particular arrangement of this invention. Three cases were involved in these experiments. FIGS. 11 and 12 represent cases A and B, respectively. FIG. 11 shows a catheter (used in case A) having the outer tube 16 provided with bores 40 at the top, bottom and both sides, totalling four bores, when the tapered surface of the needle 4 is faced upward. Case B differed from case A in that the bore located at the top portion of the outer tube 16 in case A was transferred to the bottom portion, namely, two bores were formed 1.1 mm apart from each other in the bottom portion in case B as seen from FIGS. 7 to 10 and 12. Further, case C differed from case B in that the bores 40 located at both sides of the outer tube in case B were transferred upward to contact the edges of the prohibitive region with θ of 30°. In any of cases A to C, the outer tube 16 was provided by a fluorinated ethylene propylene resin tube having an inner diameter of 2.03 mm and an outer diameter of 2.43 mm, with the length of the tapered portion being 8.00 mm. The resin tube was provided with circular bores each sized at 1.1 mm in diameter and extending through the wall thereof.

In each case of the experiments, the catheter was inserted through a wet deer hide 28a having a thickness of 0.54 mm at a speed of 30 mm/min so as to measure the maximum resistance of the hide to the catheter insertion. Incidentally, the catheter was inserted at an angle of 30° with the wet deer hide 28a. The following table shows the results of the experiments. Each of the values shown in the table represents the average of 20 samples.

| Case | Results of Experiments Maximum Resistance to Catheter Insertion |
|---|---|
| A | 912 (g) |
| B | 605 (g) |
| C | 731 (g) |

The above table shows that the insertion capability of a catheter is markedly influenced by the location of the bore. In case A, some of the catheter samples were caught by the hide at the bores, rendering it impossible to insert the catheters through the hide.

As seen from the experiments described above, it is important to select properly the location of the bore in order to reduce the resistance to the catheter insertion into a blood vessel and the pain given to the patient. In addition, the bore can not be broken if properly located. Further, the properly located side bore is scarcely closed by the wall of a blood vessel when the catheter is kept stuck to the blood vessel.

Incidentally, it is preferred to use a highly flexible plastic material such as TFE (tetrafluoroethylene) resin or FEP (fluorinated ethylene propylene) resin for forming each of the inner and outer tubes of the double-walled tube 3.

The needle 4 provided by, for example, a stainless steel tube is removably inserted through the elastic sealing member 6 into the central passageway formed in the inner tube. As shown in FIG. 1, the tip of the needle is sharpened so as to facilitate inserting into a blood vessel and the base of the needle is provided with a head 25. Further, a cap 27 equipped with a water-repelling filter 26 serving to withdraw the air from the needle is mounted to the head 25. When the needle 4, which is hollow, has been inserted into a blood vessel of the patient, the blood flows into the head 25 of the needle. Thus, it is preferred to use a transparent material for forming each of the head 25 and the cap 27. Namely, the blood introduced into the head can be recognized through the transparent material, rendering it possible to confirm the sticking of the tip of the needle into a blood vessel.

Figure 3:
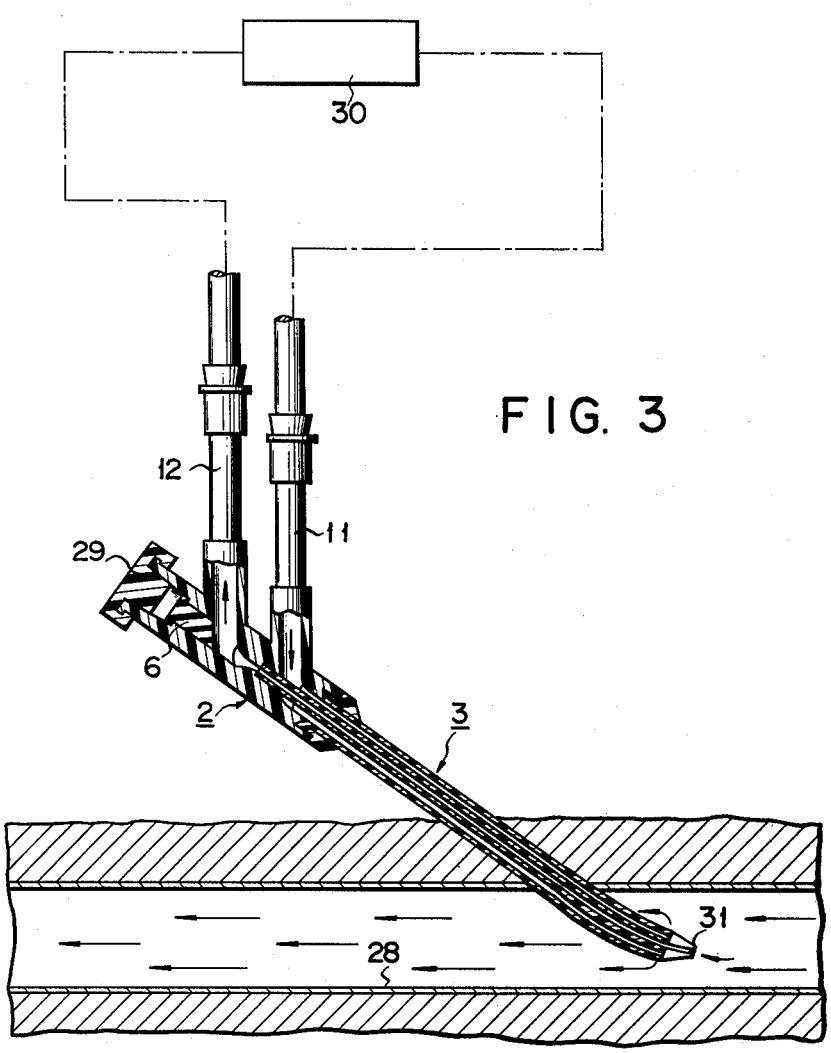
FIG. 3 is a view with parts broken away and in section of a vascular channel with catheter embodying the invention being inserted therein.

FIG. 3 shows how to use the intravascular catheter of the construction described above. Specifically, the sharpened tip of the needle 4 is inserted into a blood vessel 28 and, then, the needle 4 alone is withdrawn with the tip portions of the inner and outer tubes 13 and 16 kept fully inserted within the blood vessel 28. As described above, the blood flows into the head 25 of the needle soon after the tip of the needle has been inserted into the blood vessel 28. Since the head 25 is formed of a transparent material, the blood introduced thereto can be readily recognized visually, rendering it possible to confirm that the tip of the needle has been inserted into the blood vessel 28.

It should be noted that the tapered tip portion of the double-walled tube 3 conforms with the sharpened tip of the needle 4 as described previously. This construction is very effective for facilitating the insertion of the tip portion of the double-walled tube into the blood vessel 28. Specifically, the outer diameter of the tip of the double-walled tube is substantially equal to that of the tip of the needle and, thus, the resistance occurring in the insertion step is rendered negligible, leading to the smooth insertion as mentioned above.

As soon as the needle 4 has been withdrawn, the hole made by the needle insertion in the sealing member 6 is collapsed by the elasticity of the sealing material, thereby preventing the blood from leaking outside through the sealing member. The sealing effect can be enhanced if an auxiliary cap 29 is mounted to the base portion of the hub upon withdrawal of the needle 4.

After the intravascular catheter has been set as shown in FIG. 3, the air within the catheter is withdrawn. Namely, the caps 9 and 10 mounted to the first and second auxiliary tubes 11 and 12, which are connected to the first and second auxiliary passageways of the hub, are removed for the air withdrawing operation. Finally, a blood dialysis circuit 30 is connected to the auxiliary tubes 11 and 12 via connecting means. It is seen that the second auxiliary tube 12 constitutes a part of the passageway of blood flowing into the dialysis circuit 30. On the other hand, the first auxiliary tube 11 constitutes a part of the returning blood passageway. It is important to note that the bores 23, 24 provided at the tip of the outer tube 16 are suitably apart from a port 31 leading to the center passageway formed in the inner tube 13. It follows that the blood returned to the blood vessel through the bores 23, 24 is prevented from entering again the dialysis circuit 30 through the port 31 as shown in FIG. 3. Incidentally, FIG. 3 shows that the double-walled tube inserted into the blood vessel 28 extends in the direction opposite to the flowing direction of the blood, however, it is possible to reverse the inserting direction of the double-walled tube.

In the latter case, the blood circulation should also be reversed, i.e., the blood should be introduced into the catheter from the bores 23, 24, and returned to the blood vessel 28 through the port 31.

As described in detail, the intravascular catheter of this invention comprises a double-walled tube provided with two separate blood passageways through which the blood is introduced into an artificial kidney or the like and is returned to the patient, respectively. It is important to note that the blood-treating circuit outside the body of the patient is rendered operable upon withdrawal of the needle stuck into a blood vessel of the patient. In other words, it suffices to stick the needle into a blood vessel only once for rendering the catheter of this invention operable. Naturally, a pain to the patient by the sticking of the needle can be markedly alleviated and the life of the shunt can be increased, as compared with the conventional catheter comprising two needles used for withdrawing and returning the blood, respectively. Further, the intravascular catheter of this invention can be used in the blood dialysis system utilizing the conventional catheter comprising two needles.

Figure 4:
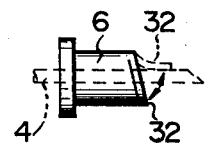
FIG. 4 is a detail view showing a modification of a sealing member to be mounted to the base portion of the hub.

The sealing member 6 mounted to the base end portion of the hub should naturally be formed of a highly flexible material. For enhancing the sealing effect, however, it is possible to employ various valve mechanisms. For example, FIG. 4 shows a flexible sheet 32 mounted to the inner edge of the sealing member 6. Naturally, the sheet 32 acts as a valve so as to prevent the blood from leaking outside through the sealing member 6.

Although the foregoing has been primarily described with respect to an intravascular catheter having a pair of auxiliary passages branched from the axial passage of the hub, it is also possible to omit the second auxiliary passageway 8 and to utilize the axial passage per se as the second auxiliary passage. FIG. 5 shows an embodiment of such a construction wherein only the second auxiliary passageway 8 and the sealing member 6 are omitted as compared with that shown in FIG. 1. Accordingly, the intravascular catheter shown in FIG. 5 comprises a hub 33 having an axial passage 34 opening at both ends, an auxiliary passageway 7 branched from the axial passageway 34, a flexible double-walled tube 3 having an inwardly tapered tip portion 21 and consisting of an inner tube 13 extending into the axial passageway 34 formed in the hub 33 and providing a central passageway 15 and an outer tube 16 disposed in coaxial with the inner tube 13, thereby forming an annular passageway 22 between the outer wall of the inner tube 13 and the inner wall of the outer tube 16, the base edge of the inner tube being secured at an intermediate inner wall of the axial passageway 34 between the auxiliary passageway 7 and the forward end of the axial passage 34, the base edge of the outer tube 16 being fixed to the forward end of the hub 33 so as to enable the annular passageway 22 to communicate with the auxiliary passageway 7, and the central passageway 15 having an opening at the tapered tip 21 of the double-walled tube 3 and the forward end of the annular passageway 20 communicated with a pair of bores 23, 24 provided at the forward end portion of the outer tube 16, and needle 4 removably inserted into the central passageway 15 formed in the inner tube 13 such that the tip of the needle 4 extends beyond the tapered tip 21 of the double-walled tube 3.

As described above, the catheter shown in FIG. 5 makes use of part of axial passage 5 as the second auxiliary passageway 8. Accordingly, in the employment of this type of catheter, upon withdrawal of the needle 4 from a vascular channel, leaving the tip of the double-walled tube kept within the channel, one end of a blood circulating tube is connected to a recessed end portion 35 of the hub 2, thereby obtaining a blood circulation equivalent to the case of an intravascular catheter shown in FIG. 1. It is also possible to preliminarily provide the recessed end portion of the hub with an elastic reseal plug.

What we claim is:

1. An intravascular catheter, comprising:
    a hub having an axial passage which is open at the forward end and sealed with a sealing member at the base end opposite to said forward end, a first auxiliary passageway branched from the axial passageway near the forward end of the hub, and a second auxiliary passageway communicating with the axial passageway at the sealed end of the axial passage;
    a flexible double-walled tube having a solid and smoothly tapered tip portion and consisting of an inner tube extending into the axial passageway formed in the hub and providing a central passageway and an outer tube disposed in coaxial relation to the inner tube and with its outer surface merging smoothly with the tapered surface of said tip portion, thereby forming an annular passageway between the outer wall of the inner tube and the inner wall of the outer tube, the base edge of the inner tube being secured at an intermediate portion between the positions from which the first and second auxiliary passageways extend outward so as to enable the central passageway formed in the inner tube to communicate with the second auxiliary passageway, the base edge of the outer tube being fixed to the forward end of the hub so as to enable the annular passageway to communicate with the first auxiliary passageway, and the central passageway having an opening at the tip of said tip portion and the forward end of the annular passageway having at least one bore provided at the forward end portion of the outer tube at the juncture of the outer tube and said tip portion; and
    a needle removably inserted into the central passageway formed in the inner tube through the sealing member provided at the base portion of the hub such that the tip of the needle extends beyond the tapered tip of the double-walled tube and defines a smooth continuation of the tapered outer surface of said tip portion, the location of said bore in the outer tube being confined to a portion which excludes a top curve portion of the outer tube in the cross section perpendicular to the axis of the catheter, which when the axis of the catheter is disposed horizontally and a tapered tip surface of the needle is faced vertically upward falls within ±30° around the center of the needle as measured from the top point of the top curve portion.

2. The intravascular catheter according to claim 1, wherein a flexible sheet acting as a valve to prevent the blood from leaking outside is mounted to the inner edge of the sealing member.

3. The intravascular catheter according to claim 1, wherein a cap provided with a water repelling filter serving to withdraw the air is mounted to the head of the needle.

4. The intravascular catheter according to claim 1, wherein four bores are formed, one at each side and two at bottom of the outer tube.

5. An intravascular catheter, comprising:
    a hub having an axial passage opening at both ends, an auxiliary passageway branched from the axial passageway;
    a flexible double-walled tube having a solid and smoothly tapered tip portion and consisting of an inner tube extending into the axial passageway formed in the hub and providing a central passageway and an outer tube disposed in coaxial relation to the inner tube and with its outer surface merging smoothly with the tapered surface of said tip portion, thereby forming an annular passageway between the outer wall of the inner tube and the inner wall of the outer tube, the base edge of the inner tube being secured at an intermediate inner wall of the axial passageway between the auxiliary passageway and the rearward end of the axial passage, the base edge of the outer tube being fixed to the forward end of the hub so as to enable the annular passageway to communicate with the auxiliary passageway, and the central passageway having an opening at the tip of said tip portion and the forward end of the annular passageway having at least one bore provided at the forward end portion of the outer tube at the juncture of the outer tube and said tip portion, said solid, smoothly and uniformly tapered tip portion being made of the same material as those of the inner and outer tubes and integrally connected with the inner and the outer tubes;
a needle removably inserted into the central passageway formed in the inner tube such that the tip of the needle extends beyond the tapered tip of the double-walled tube and defines a smooth continuation of the tapered outer surface of said tip portion, the location of said bore in the outer tube being confined to a portion which excludes a top curve portion of the outer tube in the cross section perpendicular to the axis of the catheter, which when the axis of the catheter is disposed horizontally and a tapered tip surface of the needle is faced vertically upward falls within $\pm 30°$ around the center of the needle as measured from the top point of the top curve portion.

6. The intravascular catheter according to claim 5, wherein four bores are formed, one at each side and two at bottom of the outer tube.

7. The intravascular catheter according to claim 5, wherein a cap provided with a water repelling filter serving to withdraw the air is mounted to the head of the needle.

8. The intravascular catheter according to claim 5, wherein four bores are formed, one at each side and two at the bottom of the outer tube.

* * * * *